United States Patent
Huang et al.

(10) Patent No.: US 6,417,407 B1
(45) Date of Patent: Jul. 9, 2002

(54) METHOD OF MAKING 2-BROMO-4-CHLORO SUBSTITUTED PHENOLS

(75) Inventors: Bao-Guo Huang, Getzville; Lawrence B. Fertel, Williamsville, both of NY (US)

(73) Assignee: Gabriel Performance Products, LLC, Baton Rouge, LA (US)

(*) Notice: Subject to any disclaimer, the term of this patent is extended or adjusted under 35 U.S.C. 154(b) by 0 days.

(21) Appl. No.: 09/502,082

(22) Filed: Feb. 10, 2000

(51) Int. Cl.$^7$ .................. C07C 45/63; C07C 67/307; C07C 51/62
(52) U.S. Cl. ................ 568/433; 560/65; 562/864
(58) Field of Search ................ 560/65; 562/864; 568/433

(56) References Cited

U.S. PATENT DOCUMENTS

| | | | |
|---|---|---|---|
| 3,621,064 A | | 11/1971 | Rosin ................. 260/600 |
| 4,190,600 A | * | 2/1980 | Landauer ............. 260/544 D |
| 4,945,186 A | * | 7/1990 | Matsuura et al. ......... 568/433 |
| 5,772,668 A | | 6/1998 | Fertel et al. ........... 568/655 |

OTHER PUBLICATIONS

Wriede et al., "Synthesis of Halodimethoxy–1,2–benzoquinones," *J. Org. Chem.*, 52, pp. 4485–4489 (1987).
Biltz et al., "On the Chlorination of Salicylaldehydes," *Berichte Der Deutschen Chemischen Gesellschaft*, pp. 4022 to 4031 (1904).
Wiley et al., "Infrared Spectra of the Nitrile N–Oxides: Some New Furoxans," *J. Org. Chem.*, 25, pp. 546 to 551, (1960).
Smirnov et al., "Structure and Color of Salicylidenaniline Derivatives Containing Additional Substituents in the Aldehyde Component," *Doklady Akademii Nauk SSSR*, 179, pp. 240 to 243 (1967).

* cited by examiner

Primary Examiner—Peter O'Sullivan
(74) Attorney, Agent, or Firm—Robert H. Earp, III; McDonald, Hopkins, Burke & Haber LLC

(57) ABSTRACT

A 2-bromo-4-chloro substituted phenol is prepared from a first composition of a substituted phenol and benzotrifluoride in a weight ratio to the substituted phenol of about 2 to about 4. Into the first composition is sparged about 1 to about 1.5 equivalents of chlorine gas, whereby the substituted phenol is chlorinated to form a 4-chloro substituted phenol. The first composition is cooled to precipitate the 4-chloro substituted phenol, which can be isolated by filtration. A second composition is formed of the 4-chloro substituted phenol, acetic acid in an weight ratio to the 4-chloro substituted phenol of about 1 to about 2, about 1 to about 2 equivalents of a salt of a strong base and a weak acid, and about 1 to about 5 equivalents of a brominating agent, whereby the 4-chloro substituted phenol is brominated to form a 2-bromo-4-chloro substituted phenol.

20 Claims, No Drawings

METHOD OF MAKING 2-BROMO-4-CHLORO SUBSTITUTED PHENOLS

BACKGROUND OF THE INVENTION

This invention relates to chlorinating then brominating a substituted phenol. In particular, it relates chlorinating salicylaldehyde (SAL) to form 5-chlorosalicylaldehyde (5CSAL), followed by brominating to form 3-bromo-5-chlorosalicylaldehyde (BCSAL).

BCSAL is an important intermediate used to make anti-cancer drugs. It is made by chlorinating SAL to form 5CSAL, followed by brominating the 5CSAL. The chlorination step has been performed neat (U.S. Pat. No. 3,621,064), in acetic acid (Chemische Beuchte, 37, 4 to 24,1904), and in chloroform (J. Org. Chem. 25, 546,1960). The bromination step in acetic acid is briefly mentioned in Smirnor, Kivichenko; Dokl. Chem. (Eng. Transl.) 179, 240, 1968). Results using prior art processes are less than satisfactory.

SUMMARY OF THE INVENTION

We have discovered that if SAL is chlorinated in a solvent of benzotrifluoride (BTF) a higher yield and an excellent purity are obtained after a simple workup. We have obtained yields of 75% and purities of over 99%. We have further found that if the bromination step is performed in a mixture of acetic acid and a strong base of a weak acid salt, such as sodium acetate, the formation of diaryl ethers, a major byproduct in the bromination reaction, is inhibited. We have obtained yields of 93% and purities of over 99.5% in the bromination step without further purification.

DESCRIPTION OF THE PREFERRED EMBODIMENTS

In the process of this invention, 2-bromo-4chloro substituted phenols are made in two steps. The first step is the chlorination of a substituted phenol to make a 4-chloro substituted phenol and the second step is the bromination of the 4-chloro substituted phenol. The overall general reaction, using sodium acetate and bromine, is as follows:

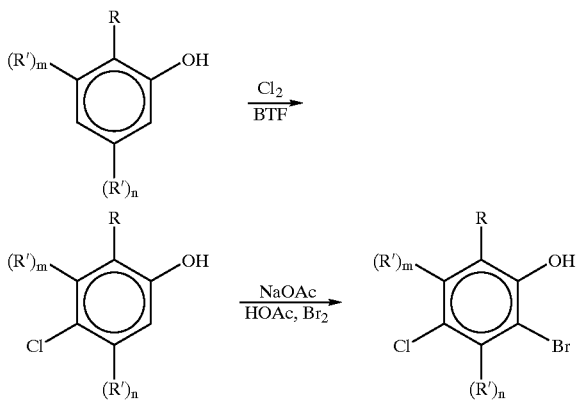

The substituted phenol has the general formula shown in the above reaction, where R is CHO, COCl, or $CO_2R''$, R'' is alkyl from $C_1$ to $C_4$, each R' is independently selected from alkyl from $C_1$ to $C_4$, m is 0 or 1, and n is 0 or 1. Preferably, R is CHO, R' is hydrogen, R'' is hydrogen, m is 0, and n is 0 as those compounds are commercially more important. Examples of compounds that can be used include SAL, phenol, and 2-chlorophenol; SAL is preferred as it is used to make BCSAL.

The substituted phenol is mixed with BTF to form a solution. The weight ratio of BTF to the substituted phenol should be about 2 to about 4 as the product may precipitate at a lower ratio and a higher ratio will reduce the throughput and may reduce the yield; the preferred weight ratio is about 2.5 to about 3.5.

Chlorine gas is sparged into the solution. About 1 to about 1.5 equivalents of chlorine gas should be used as more may result in higher chlorinated products and less will leave unreacted substituted phenol. The preferred amount of chlorine gas is about 1.1 to about 1.2 equivalents. The reaction is exothermic and can be started at room temperature. The temperature can then be permitted to rise to about 50 to about 80° C. The reaction is slow at lower temperatures and higher temperatures may produce more byproducts; the preferred temperature range is about 50 to about 60° C. The reaction can be followed by performing gas chromatography (GC) on samples or by checking the amount of chlorine gas feed. When the reaction is complete, the 4-chloro substituted phenol is isolated. If the product is 5CSAL, the mixture can be cooled to about 50° C., which precipitates the 5CSAL. The 5CSAL can then be isolated by, for example, filtration. High purity (GC>99%) product can be obtained after washing twice with BTF.

In the bromination step, the 4-chloro substituted phenol is mixed with acetic acid and a salt of a strong base and a weak acid. The weight ratio of acetic acid to the 4-chloro substituted phenol is about 1 to about 5 as more acetic acid will reduce throughput and, if less is used, the mixture will be hard to stir; the preferred weight ratio is about 2 to about 3. Examples, of salts of a strong base and a weak acid that can be used include sodium acetate, potassium acetate, sodium carbonate, sodium phosphate, and sodium oxalate. The preferred salt is sodium acetate because it works well and produces additional acetic acid when it reacts. About 1 to about 2 equivalents of the salt should be used as less will result in less conversion and more is unnecessary.

Brominating agents that can be used include liquid bromine, a mixture of hydrogen bromide and hydrogen peroxide in an equimolar ratio or a mixture of hydrogen bromide and sodium hypochlorite in an equimolar ratio. The preferred brominating agent is liquid bromine as it has been found to work well. About 1 to about 1.5 equivalents of the brominating agent should be used as less will result in incomplete conversion and more may result in overbromination. Preferably, about 1.05 to about 1.2 equivalents of the brominating agent are used.

The bromination reaction is exothermic and cooling is usually necessary. The temperature should be kept below about 35° C. to prevent overbromination. A temperature of about 25 to about 35° C. is preferred. The reaction can be followed by analyzing samples using GC. When the reaction is complete, water can be added, which will precipitate the brominated product. The mixture can be cooled to about 5° C. and the product can be collected by, for example, filtration, then washed with water to remove any acetic acid. The purity of the product is usually over 99%.

The following examples further illustrate this invention:

EXAMPLE 1

Chlorination of SAL in BTF

SAL (502.9 g, 4.12 mol) was mixed with BTF (1.48 L) and the resulting solution was heated to 50° C. while purging with nitrogen. After 20 min, chlorine gas was slowly introduced into the solution to maintain the temperature below 60° C. The reaction mixture was charged with 310.9 g of chlorine (1.06 equiv.), then cooled to 5° C. The crystals were collected by vacuum filtration and washed with cool BTF (2×300 mL). 507.9 g (78.6%) of 5CSAL was obtained with GC purity over 99.0%.

EXAMPLE 2

Chlorination of SAL in BTF

Example 1 was repeated using 2.00 kg (16.39 mol) of SAL, 6.0 L of BTF, and 1.43 kg of chlorine (1.23 equiv.). After washing with cool BTF (2×1.2 L), 1.93 kg (75.4%) of 5CSAL was obtained with a GC purity of 99.3%.

EXAMPLE 3

Bromination of 5CSAL in Acetic Acid and Sodium Acetate

To a suspension of 5CSAL (292 g, 1.87 mol) and sodium acetate (153 g, 1.0 equiv.) in acetic acid (800 mL) at room temperature was slowly added bromine (96.3 mL, 1.1 equiv.). After the addition was complete (1 hr), the mixture was stirred for another 30 min. Water (300 mL) was added to the mixture to precipitate the product. The mixture was cooled to 5° C and crystals were collected by vacuum filtration. After washing with water (2×150 mL), the crystals were dried at 40° C. for 4 hrs. 381.1 g of BCSAL (86.8) was obtained (GC purity:99.4%).

EXAMPLE 4

Bromination of 5CSAL in Acetic Acid and Sodium Acetate

Example 3 was repeated using a suspension of 1.45 kg (9.29 mol) of 5CSAL and 801.3 g (1.05 equiv.) of sodium acetate in 2.5 L of acetic acid at room temperature, to which was slowly added 501.3 mL (1.05 equiv.) of bromine. After the addition was complete (1.5 hrs), the mixture was stirred for another 30 min. Water (2.0 L) was added to the mixture to precipitate the product. The mixture was cooled to 5C and crystals were collected by vacuum filtration. After washing with water (2×1.2 L), the crystals were dried at 40° C. for 4 hrs. 1.99 kg of BCSAL (91.5%) was obtained (GC purity:99.5%).

EXAMPLE 5

Comparison-Bromination of 5CSAL in Acetic Acid in the Absence of Sodium Acetate

To a suspension of 5CSAL (73.3 g, 0.47 mol) in acetic acid (300 mL) at room temperature was slowly added bromine (82.9 g, 1.1 equiv.). After stirring at room temperature for 4.0 hrs, the reaction mixture contained 80.5% desired product, 8.64% diaryl ethers, and 9.7% unreacted starting material by GC analysis. Water was added to precipitate the product. The isolated crude product was purified by recrystallization from BTF (90 mL). 76.2 g of BCSAL (68.9%) was obtained with a GC purity of 97.8%.

EXAMPLE 6

Comparison-Bromination of 5CSAL in 90% Acetic Acid in the Absence of Sodium Acetate Example 5 was repeated using a suspension of 14.75 g (9.4 mmol) 5CSAL in 54 mL acetic acid and 6 mL water at room temperature, to which was slowly added 16.6 g (1.1 equiv.) of bromine. After stirring at room temperature for 3.5 hrs, the GC yield of BCSAL was 88.2% along with 8.4% unreacted starting material. No diaryl ethers were detected on GC. Stirring was continued for another 4 hrs, but no further reaction was observed.

We claim:

1. A method of making a 2-bromo4-chloro substituted phenol having the general formula

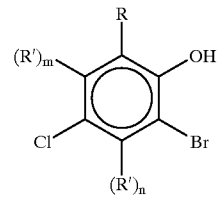

comprising
(A) preparing a first composition which comprises
(1) a substituted phenol having the general formula

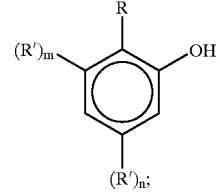

and
(2) benzotrifluoride in a weight ratio to said substituted phenol of about 2 to about 4;
(B) sparging into said first composition about 1 to about 1.5 equivalents of chlorine gas, whereby said substituted phenol is chlorinated to form a 4-chloro substituted phenol having the general formula

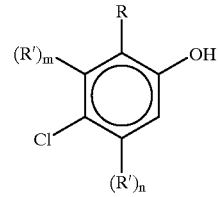

(C) cooling said first composition to precipitate said 4-chloro substituted phenol;
(D) isolating said 4-chloro substituted phenol; and
(E) forming a second composition which comprises
(1) said 4-chloro substituted phenol;
(2) acetic acid in an weight ratio to said 4chloro substituted phenol of about 1 to about 5;
(3) about 1 to about 2 equivalents of a salt of a strong base and a weak acid; and
(4) about 1 to about 2 equivalents of a brominating agent, where R is CHO, COCl, or $CO_2R''$, R" is alkyl from $C_1$ to $C_4$, each R' is independently selected from alkyl from $C_1$ to $C_4$, m is 0 or 1, and n is 0 or 1.

2. A method according to claim 1 wherein R is CHO.

3. A method according to claim 1 wherein R' is methyl and n is 1.

4. A method according to claim 1 wherein R' is methyl and m is 1.

5. A method according to claim 1 wherein m is 0 and n is 0.

6. A method according to claim 1 wherein said substituted phenol is salicylaldehyde.

7. A method according to claim 1 wherein the temperature of said first composition is between 50 and 80° C. during step (B).

8. A method according to claim 7 wherein the temperature of said first composition is between 50 and 60° C. during step (B).

9. A method according to claim 1 wherein the temperature of said second composition is kept below 35° C. during step (E).

10. A method according to claim 9 wherein the temperature of said second composition is about 25 to about 30° C. during step (E).

11. A method according to claim 1 wherein said brominating agent is liquid bromine.

12. A method according to claim 1 wherein said salt of a strong base and a weak acid is sodium acetate.

13. A method according to claim 1 wherein the weight ratio of said benzotrifluoride is about 2.5 to about 3.5.

14. A method according to claim 1 wherein the equivalents of said chlorine gas are about 1. to about 1.2.

15. A method of chlorinating salicylaldehyde comprising
(A) preparing a composition which comprises
  (1) salicylaldehyde; and
  (2) benzotrifluoride in a weight ratio to said salicylaldehyde of about 2 to about 4;
(B) sparging into said composition about 1 to about 1.5 equivalents of chlorine gas;
(C) maintaining the temperature of said composition between about 50 to about 80° C.;
(D) cooling said composition to precipitate 5-chlorosalicylaldehyde; and
(E) isolating said 5-chlorosalicylaldehyde by filtration.

16. A method according to claim 15 wherein the temperature of said composition is between 50 and 60° C. during step (C).

17. A method according to claim 15 wherein said 5-chlorosalicylaldehyde is brominated by
(A) forming a second composition which comprises
  (1) said 5-chlorosalicylaldehyde;
  (2) acetic acid in an weight ratio to said 5-chlorosalicylaldehyde of about 1 to about 5;
  (3) about 1 to about 2 equivalents of sodium acetate; and
  (4) about 1 to about 2 equivalents of liquid bromine; and
(B) maintaining the temperature of said second composition below 35° C.

18. A method according to claim 17 wherein the temperature of said second composition in step (B) is maintained at about 25 to about 30° C.

19. A method of brominating 5-chlorosalicylaldehyde comprising
(B) forming a composition which comprises
  (1) 5-chlorosalicylaldehyde;
  (2) acetic acid in an weight ratio to said 5-chlorosalicylaldehyde of about 1 to about 5;
  (3) about 1 to about 2 equivalents of sodium acetate; and
  (4) about 1 to about 2 equivalents of liquid bromine; and
(B) maintaining the temperature of said composition below about 35° C.

20. A method according to claim 19 wherein the temperature of said composition is maintained at about 25 to about 30° C.

* * * * *